(12) United States Patent
Khait

(10) Patent No.: US 11,918,343 B2
(45) Date of Patent: Mar. 5, 2024

(54) SYSTEM AND METHOD FOR POSITION DETECTION OF AN IN-VIVO DEVICE

(71) Applicant: GIVEN IMAGING LTD., Yoqneam (IL)

(72) Inventor: Semion Khait, Tiberias (IL)

(73) Assignee: GIVEN IMAGING LTD., Yoqneam (IL)

( * ) Notice: Subject to any disclaimer, the term of this patent is extended or adjusted under 35 U.S.C. 154(b) by 748 days.

(21) Appl. No.: 16/493,655

(22) PCT Filed: Mar. 15, 2018

(86) PCT No.: PCT/IL2018/050305
§ 371 (c)(1),
(2) Date: Sep. 12, 2019

(87) PCT Pub. No.: WO2018/167793
PCT Pub. Date: Sep. 20, 2018

(65) Prior Publication Data
US 2020/0022614 A1    Jan. 23, 2020

Related U.S. Application Data

(60) Provisional application No. 62/472,146, filed on Mar. 16, 2017.

(51) Int. Cl.
| | |
|---|---|
| *A61B 5/07* | (2006.01) |
| *A61B 1/04* | (2006.01) |
| *A61B 5/00* | (2006.01) |
| *A61B 5/06* | (2006.01) |
| *H04W 56/00* | (2009.01) |

(52) U.S. Cl.
CPC .............. *A61B 5/073* (2013.01); *A61B 1/041* (2013.01); *A61B 5/061* (2013.01); *H04W 56/00* (2013.01); *A61B 5/6861* (2013.01); *A61B 2562/0238* (2013.01)

(58) Field of Classification Search
CPC . A61B 2034/2055; A61B 6/547; A61B 5/061; A61B 5/6861; A61B 5/6851; A61B 5/073
See application file for complete search history.

(56) References Cited

U.S. PATENT DOCUMENTS 6,273,904 B1 *  8/2001  Chen ...................... A61N 5/062
606/14
7,009,634 B2   3/2006  Iddan et al.
(Continued)

OTHER PUBLICATIONS

First Office Action issued in corresponding Chinese applicaiton 201880015545.6 dated Jul. 22, 2021 (Chinese language) (5 pages).
(Continued)

*Primary Examiner* — Oommen Jacob
(74) *Attorney, Agent, or Firm* — Carter, DeLuca & Farrell LLP

(57) ABSTRACT

A system and method for detecting the position of an in-vivo device based on external light: the system may include an in-vivo device configured for being introduced into a body and having at least one sensor configured for sensing light; and an ex-vivo module including at least one illumination source configured for emitting an indication light towards said body; the indication light is configured for being sensed by the at least one sensor.

13 Claims, 8 Drawing Sheets

(56) References Cited

U.S. PATENT DOCUMENTS

| | | | |
|---|---|---|---|
| 7,016,714 B2* | 3/2006 | Colvin, Jr. | G01N 21/6428 600/316 |
| 7,118,529 B2* | 10/2006 | Glukhovsky | A61B 5/14539 600/160 |
| 8,540,623 B2 | 9/2013 | Blijevsky | |
| 8,731,637 B2* | 5/2014 | Kawano | A61B 34/73 600/417 |
| 10,531,788 B2* | 1/2020 | Wang | A61B 1/041 |
| 2004/0176669 A1* | 9/2004 | Colvin, Jr. | G01N 33/54373 128/903 |
| 2004/0199073 A1* | 10/2004 | Ma | A61B 5/06 600/595 |
| 2004/0249245 A1* | 12/2004 | Irion | A61B 5/0084 600/179 |
| 2005/0029437 A1* | 2/2005 | Hasegawa | G02B 23/2407 250/226 |
| 2005/0043583 A1* | 2/2005 | Killmann | A61B 1/041 600/109 |
| 2005/0043634 A1* | 2/2005 | Yokoi | A61B 5/0031 128/903 |
| 2005/0049488 A1* | 3/2005 | Homan | A61B 1/041 600/407 |
| 2005/0228299 A1* | 10/2005 | Banet | A61B 5/1455 600/323 |
| 2006/0036164 A1* | 2/2006 | Wilson | A61B 5/06 600/424 |
| 2006/0169293 A1* | 8/2006 | Yokoi | A61B 1/00158 128/899 |
| 2006/0173498 A1* | 8/2006 | Banville | A61N 1/37211 607/5 |
| 2006/0195014 A1* | 8/2006 | Seibel | A61B 1/0008 600/102 |
| 2007/0002038 A1* | 1/2007 | Suzuki | A61B 5/065 345/419 |
| 2007/0066868 A1* | 3/2007 | Shikii | A61B 5/073 600/118 |
| 2007/0118018 A1* | 5/2007 | Gilad | A61B 1/051 600/176 |
| 2008/0051633 A1* | 2/2008 | Blijevsky | A61B 1/041 600/117 |
| 2008/0119740 A1* | 5/2008 | Iddan | A61B 5/0084 356/300 |
| 2008/0228066 A1* | 9/2008 | Waitzman | A61B 90/30 600/424 |
| 2009/0012369 A1* | 1/2009 | Robinson | A61B 1/000094 600/182 |
| 2009/0046821 A1* | 2/2009 | Shigemori | A61B 1/041 340/5.1 |
| 2009/0124874 A1* | 5/2009 | Gono | A61B 5/6861 424/9.1 |
| 2009/0182224 A1* | 7/2009 | Shmarak | A61B 6/504 600/424 |
| 2010/0312128 A1* | 12/2010 | Karst | A61B 5/6846 600/506 |
| 2011/0166442 A1* | 7/2011 | Sarvazyan | A61B 34/20 600/424 |
| 2011/0319727 A1 | 12/2011 | Ishihara | |
| 2012/0238812 A1 | 9/2012 | Blijevsky | |
| 2013/0027267 A1* | 1/2013 | Homan | A61B 1/00016 343/893 |
| 2013/0046150 A1* | 2/2013 | Devanaboyina | A61B 5/369 600/382 |
| 2013/0237774 A1* | 9/2013 | Schentag | A61B 5/14507 600/301 |
| 2013/0289558 A1* | 10/2013 | Reid, Jr. | A61B 18/1477 606/41 |
| 2014/0031642 A1 | 1/2014 | Kimchy et al. | |
| 2015/0011829 A1* | 1/2015 | Wang | A61B 1/045 600/118 |
| 2015/0297066 A1* | 10/2015 | Yanagidate | A61B 1/041 600/109 |
| 2017/0340243 A1* | 11/2017 | Jain | A61B 5/0084 |
| 2019/0329045 A1* | 10/2019 | Cao | A61B 5/352 |
| 2020/0022614 A1* | 1/2020 | Khait | H04W 56/00 |

OTHER PUBLICATIONS

Second Office Action issued in corresponding Chinese Application No. 201880015545.6 dated Dec. 22, 2021 (Chinese language only) (6 pages).

\* cited by examiner

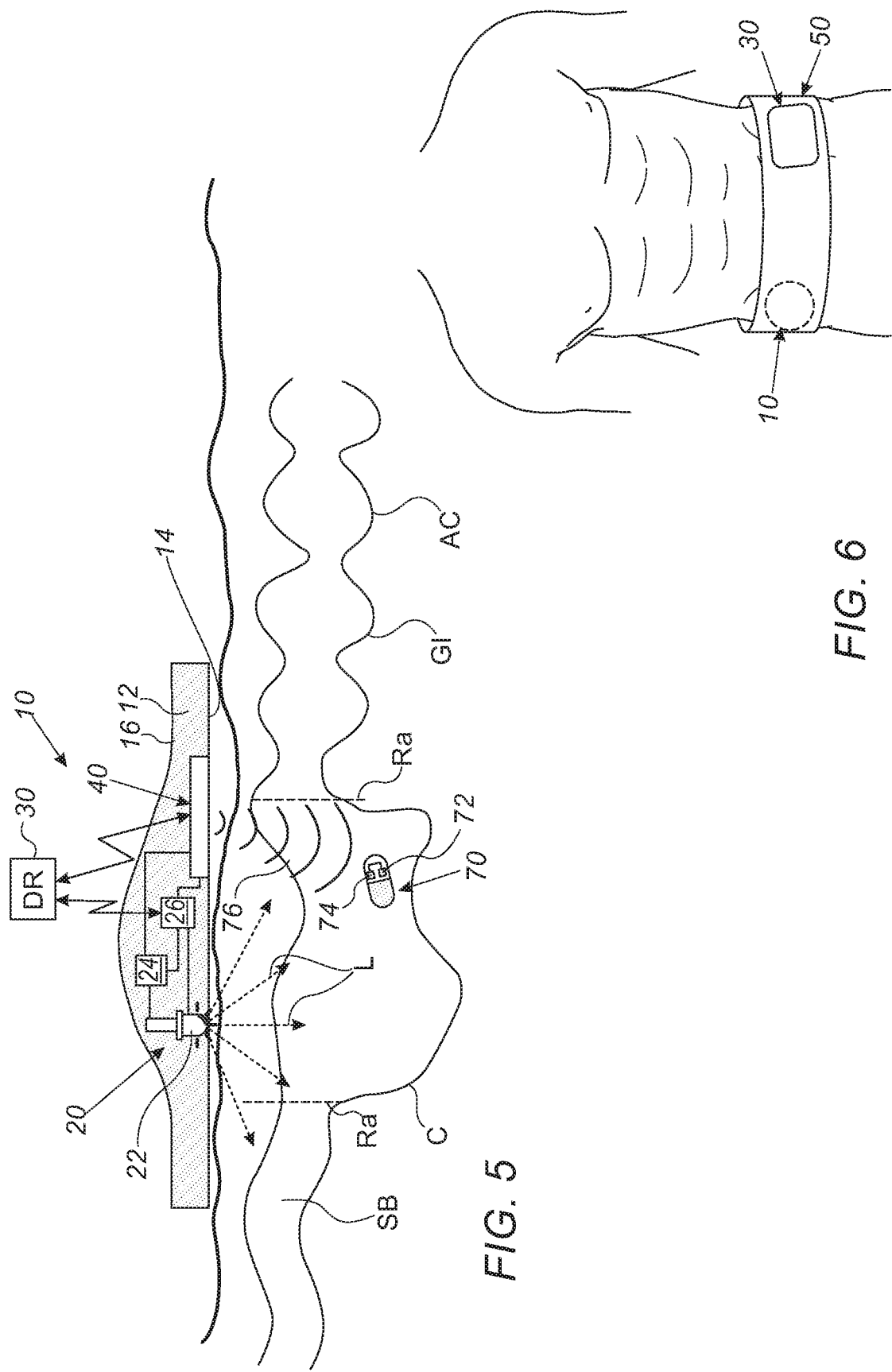

SYSTEM AND METHOD FOR POSITION DETECTION OF AN IN-VIVO DEVICE

CROSS-REFERENCE TO RELATED APPLICATIONS

This application is a National Phase Application of PCT International Application No. PCT/IL2018/050305, International Filing Date Mar. 15, 2018, claiming the benefit of U.S. Provisional Patent Application No. 62/472,146, filed Mar. 16, 2017 which are hereby incorporated by reference.

TECHNOLOGICAL FIELD

The present invention is in the field of in-vivo imaging, in particular, systems configured for detecting the position of an in-vivo device based on sensing external light.

BACKGROUND OF THE INVENTION

Swallowable in-vivo devices are well known for diagnosis of the gastrointestinal (GI) tract. A common design of such devices is a swallowable capsule which includes an outer shell having at least one transparent region (usually a dome of the shell), and an imaging system received or contained within the shell and configured for obtaining in-vivo images of the GI tract while passing through it. These images are stored on a storage device within the capsule itself (to be later retrieved) or, more commonly, are transmitted from the capsule to an external data recorder.

Many of these capsules include communication means through which the external data recorder can not only obtain the images taken by the imaging system, but also receive additional information regarding the capsule, for example, its position along the GI tract.

One example of such a capsule can include an imaging system and an ultra-low power radio frequency transmitter for transmitting signals from the CMOS imaging camera to a receiving system located outside a patient. Embodiments of the imaging system may include at least one CMOS imaging camera, at least one illumination source for illuminating an in vivo site and an optical system for imaging the in vivo site onto the CMOS imaging camera.

Acknowledgement of the above references herein is not to be inferred as meaning that these are in any way relevant to the patentability of the presently disclosed subject matter.

SUMMARY

In accordance with one aspect of the present application there is provided a system for detecting the position of an in-vivo device based on external light, said system including an in-vivo device for being introduced into a body and having at least one sensor configured for sensing light, and an ex-vivo module comprising at least one illumination source configured for emitting an indication light towards said body to be sensed by said at least one sensor.

The ex-vivo module can be configured for being fitted externally to a patient's body. In particular, the ex-vivo module can be configured for being fitted to the skin such that the at least one illumination source is directed inwards towards the body.

The ex-vivo module may constitute a part of a device to be manipulated by an operator, such as a handle, a rod etc. Alternatively, the ex-vivo module can be part of a stationary device configured for accommodating the patient, similar to an x-ray or MRI machine.

In accordance with another example, the ex-vivo module may be in the form of a patch configured for being placed against the skin. The patch can be connected to external devices in a wired or wireless manner. The patch can have a contact surface configured for facing the body when fitted thereto, and said illumination source can have at least one light emitting point located on said contact surface.

The in-vivo device may include a communication module configured for receiving alert signals from and/or transmitting alert signals to an ex-vivo device/location. The communication module may be configured for transmitting/receiving said alert signals at least upon detection of said indication light.

The ex-vivo module may be fitted to the body at a predetermined location, whereby transmitting/receiving said alert signals by the in-vivo device indicates a position of the in-vivo device inside the body corresponding to the position of the ex-vivo module.

The in-vivo device may include an imager configured for obtaining in-vivo images. The in-vivo device can be configured for obtaining said in-vivo images in a first operational mode and for switching to obtaining said in-vivo images in a second operational mode when said sensor detects said indication light. The operational modes may differ from one another, inter alia, in the frame rate of capturing images and/or the resolution of the images. Alternatively, the in-vivo device may be configured for commencing imaging upon detection of the indication light by said sensor. In this case, the difference between modes is on/off.

In addition, the in-vivo device may have an on-board (e.g. part of the in-vivo device, or internal to the in-vivo device) illumination source configured for providing light for obtaining images by the imager. Furthermore, the on-board illumination source and the illumination source of the ex-vivo module may be synchronized such that their lighting time does not fully overlap. This may be performed in order for the images obtained by the imager of the in-vivo module (facilitated by the on-board illumination source) to not be affected by the external light provided by the illumination source of the ex-vivo module (e.g. over/under exposure).

Synchronization between the light sources can be performed, for example, by:
- if the illumination source of the ex-vivo module is predetermined (i.e., not controllable), and sending out a burst of light at a given rate, the imager of the in-vivo module can be configured, once sensing the light of the ex-vivo module, to match its imaging rate to that of the illumination source of the ex-vivo module, but at an offset, so that imaging takes place only upon lighting of the on-board illumination source (and not the illumination source of the ex-vivo module); and
- if both the illumination source of the ex-vivo module and the on-board illumination source of the in-vivo module are controllable (e.g. by an external component such as a data recorder), then such an external component can actively synchronize the illumination of the two sources.

The system can further include a progress regulating component configured for slowing down and/or stopping the in-vivo device at a certain location. For example, the progress regulating component can be configured for using magnetic forces to perform said slowing down/stopping. The progress regulating component can also constitute a part of the ex-vivo module.

The progress regulating component may be used if the location of the patch corresponds to a portion of the GI tract in which the movement of the in-vivo module may be expected to be faster. In particular, under one example of the present application, the patch can be placed at a location roughly corresponding to McBurney's point, a point located ⅓ of the way between the navel and the hip bone, and indicative of the location of the appendix (and consequently, the cecum). Thus, positioning the ex-vivo module there, may also give an indication to the position of the cecum. Since in the cecum (after leaving the small bowel), the in-vivo module is expected to progress considerably faster, the progress regulating component may facilitate slowing the in-vivo module specifically there.

In accordance with another aspect of the subject matter of the present application, there is provided a method for detecting the position of an in-vivo device based on external light using, for example, the system of the previous aspect (or another system), the method including, when said in-vivo device is located within the body:

fitting said ex-vivo module to the body of the patient;
illuminating said body with said indication light; and
detecting said indication light using the sensor of said in-vivo device.

An embodiment may also include receiving/transmitting alert signals to/from said in-vivo device once said indication light is detected.

In accordance with one example of the above, an embodiment may also include obtaining said in-vivo images in a first operational mode before detection of said indication light, and switching to obtaining said in-vivo images in a second operational mode upon such detection.

According to yet another aspect of the present invention, there is provided an ex-vivo module constituting a part of the system (e.g., of the previous aspect of the present application), wherein said ex-vivo module includes an operative surface configured for facing a patient when fitted thereto, and at least one illumination source configured for emitting an indication light at a predetermined wavelength range, wherein said illumination source is facing in the same direction as the contact surface.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 5 is a schematic cross-section view of the GI tract shown in FIGS. 4A to 4D, fitted, externally, with another example of the ex-vivo module including a progress regulation component, according to an embodiment of the present invention; and FIG. 6 is a schematic front view of a monitoring belt comprising the ex-vivo module and additional devices, when mounted onto a human torso, according to an embodiment of the present invention.

Figure 1A:
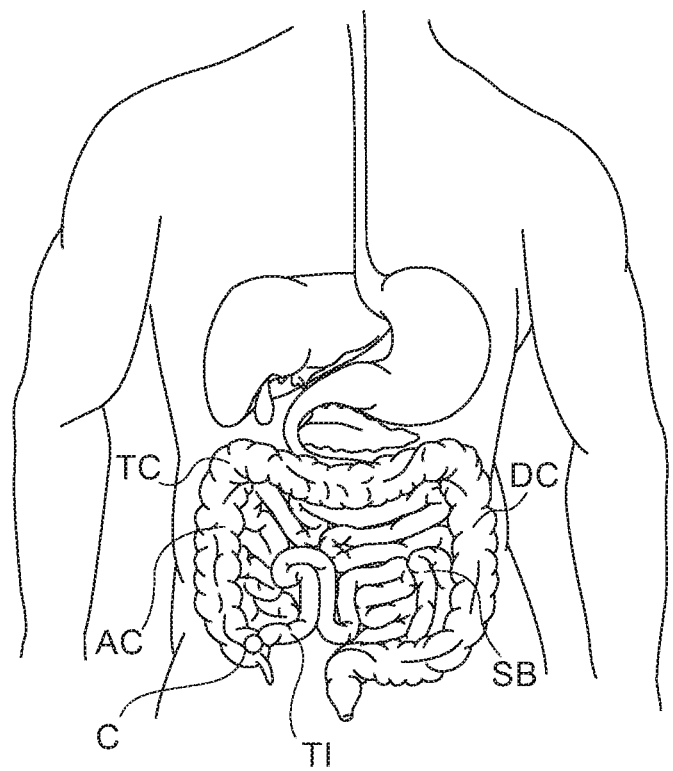
FIG. 1A is a schematic view of the human digestive system.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Figure 2A:
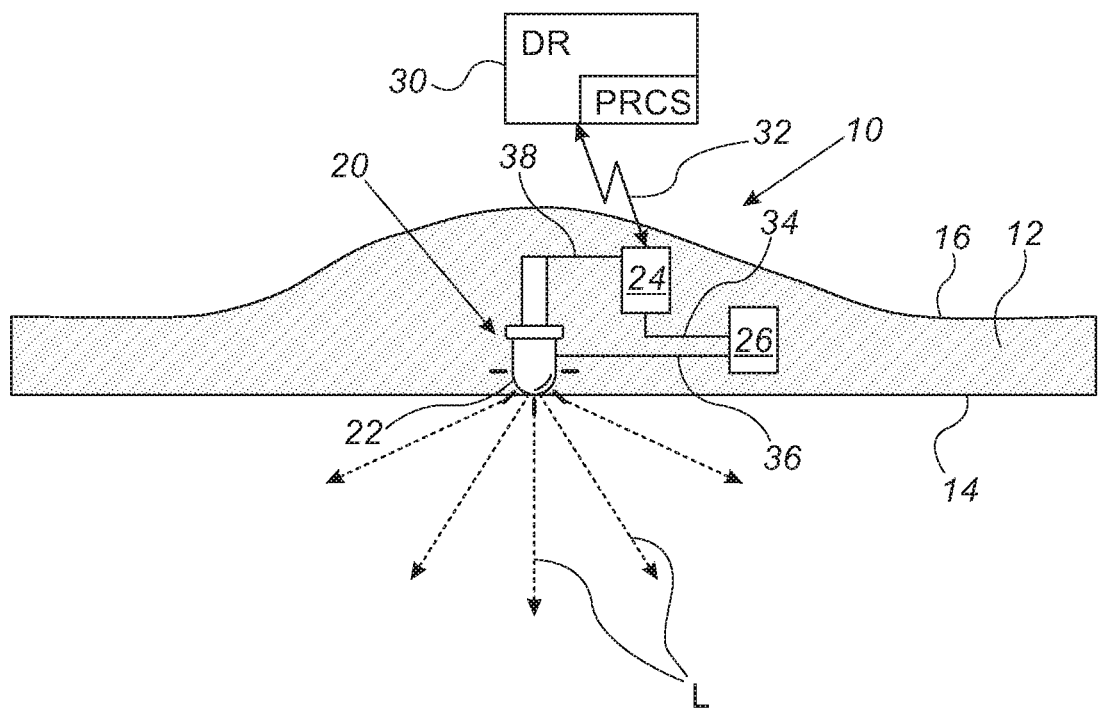
FIG. 2A is a schematic cross-section view of an ex-vivo module in accordance with one example embodiment of the subject matter of the present application.

Attention is first drawn to FIG. 2A, in which an ex-vivo module in accordance with an embodiment is shown, generally designated as 10, in the form of a patch 12 incorporating therein a functional arrangement 20 comprising an illumination source such as an LED 22 operated by a communication unit 24 via a LED control line 38, both LED 22 and communication unit 24 being powered by a power source 26 such as a battery, via connections 34 and 36 respectively. The communication unit 24 is configured for transmitting signals and/or data to a data recorder 30 in a wireless (e.g. via radio waves) manner 32. The LED 22 (or an alternative appropriate illumination source) may emit an indication light towards the body in which an in-vivo device is introduced.

Figure 2B:
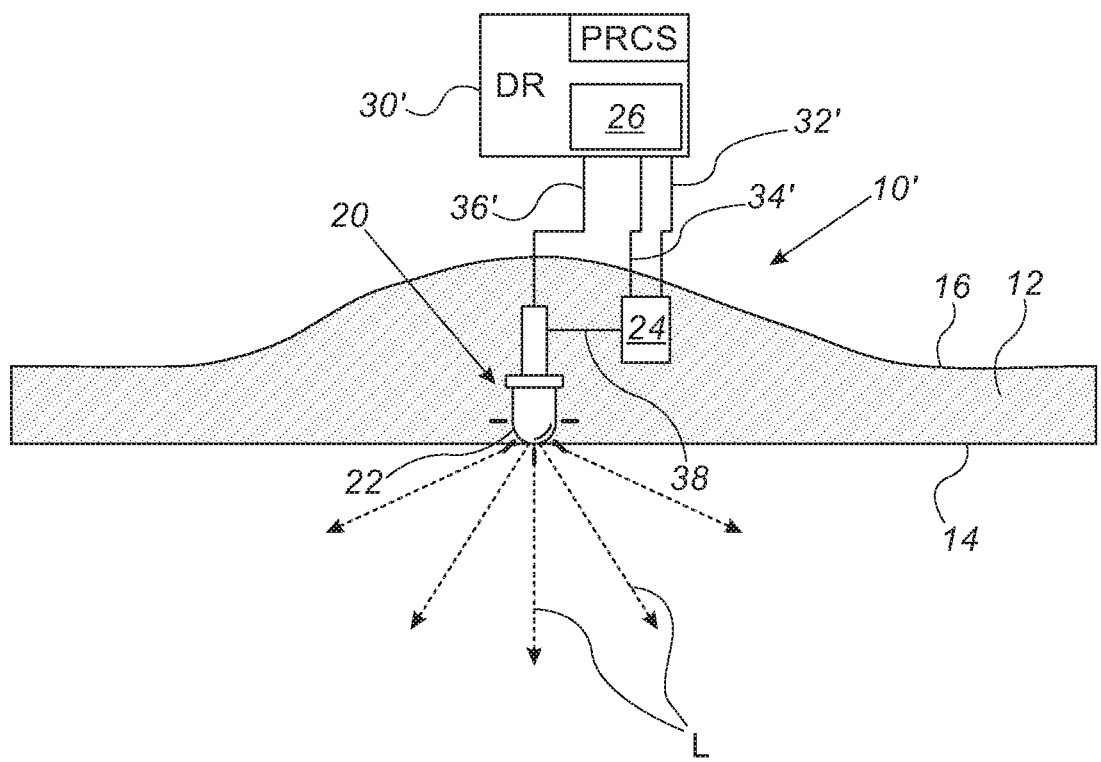
FIG. 2B is a schematic cross-section view of an ex-vivo module in accordance with another example embodiment of the subject matter of the present application.

Another example of the ex-vivo module is shown in FIG. 2B, in which the power source 26 resides in the data recorder 30 (or can be in any other device external to the ex-vivo module 10), so that the communication unit 24 and LED 22 are powered thereby via connections 34', 36' respectively. In addition, the communication unit 24 is configured for transferring data to the data recorder 30' via a wired connection 32' (instead of wireless as in the previous example). It should be appreciated that different combinations of the arrangements shown in FIGS. 2A and 2B are applicable (e.g. power source 26 is within the patch 12 while the connection 32' is wired, power source 26 is external and connection is wireless etc.)

The patch 12 is formed with an inner contact surface 14 configured for being placed against a designated area (e.g.

the skin of a patient), and an external surface 16. The LED 22 is located proximal to the contact surface 14 so that, when the patch 12 is fitted or attached (e.g. externally) to the designated surface, light rays L emitted from the LED 22 are directed towards the designated surface. Specifically, if the patch 12 is fitted to the skin of a patient (e.g. by adhesion, as common in skin-placed sensors/patches), the light rays L are directed into the patient through his/her skin S (shown in FIGS. 4A to 4D).

Turning now to FIGS. 3A to 3D, the ex-vivo module 10 may be a part of a monitoring/detection system which also includes an in-vivo device such as a capsule 70 (e.g. and endoscopic capsule), which is shown in the figures as progressing through the GI tract. In its most basic configuration, the capsule 70 includes a light sensor, e.g. an imager, such as a CMOS (complementary metal-oxide-semiconductor) or CCD (charge-coupled device, configured for detecting the light L emitted by the LED 22 of the ex-vivo module 10, and a transmitter (which is a part of the communication unit 24) configured for sending out an alert signal once light L is detected by the sensor. The alert signal is configured for being received by a data recorder DR which is usually a stand-alone device separate from the patch 12.

It is important to note that while the examples given here refer to a gastrointestinal use, embodiments of the present invention are applicable to a combination of an in-vivo device configured for sensing light external to the body.

It is appreciated that, in its most basic configuration, the monitoring system including the ex-vivo module 10 and the in-vivo device 70, can provide an indication to the position of the in-vivo device within the GI tract, or, more precisely, indicate when the in-vivo device 70 has reached a given location within the GI tract. The basic configuration will now be described with respect to FIGS. 3A to 3D, and modifications and expansions will be discussed thereafter.

Figure 3A:
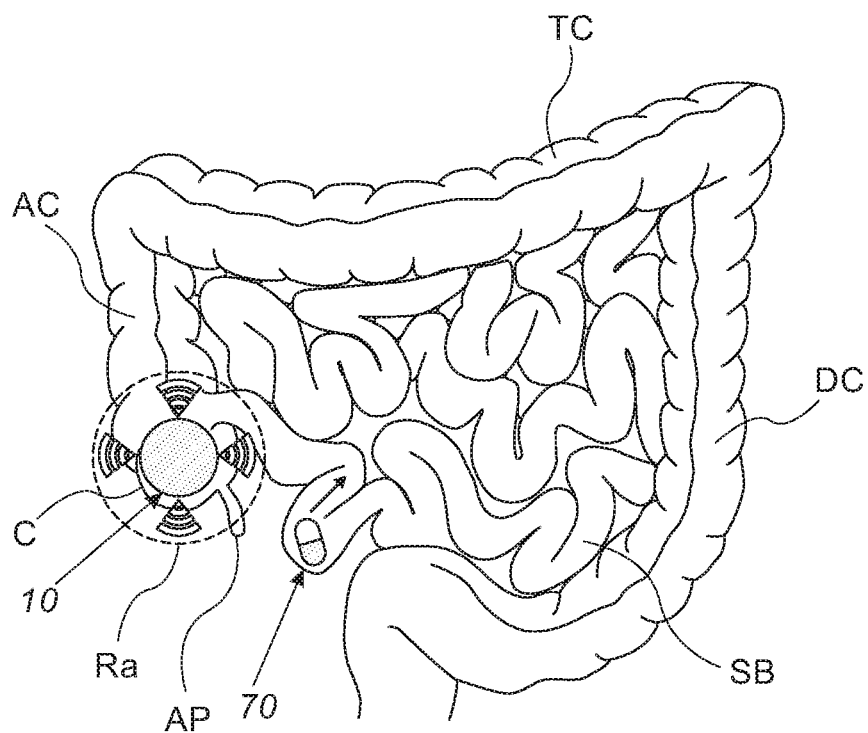
FIGS. 3A to 3D are schematic illustration of a portion of the human digestive system, shown in different stages of progression of an in-vivo device therethrough, according to an embodiment of the present invention.
Figure 3B:
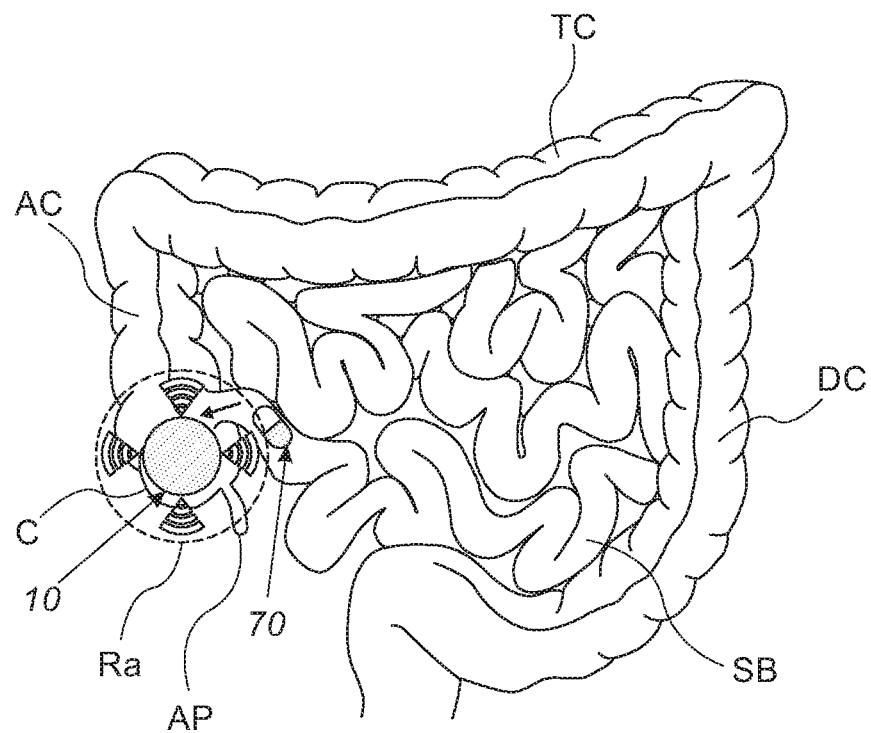
Figure 3C:
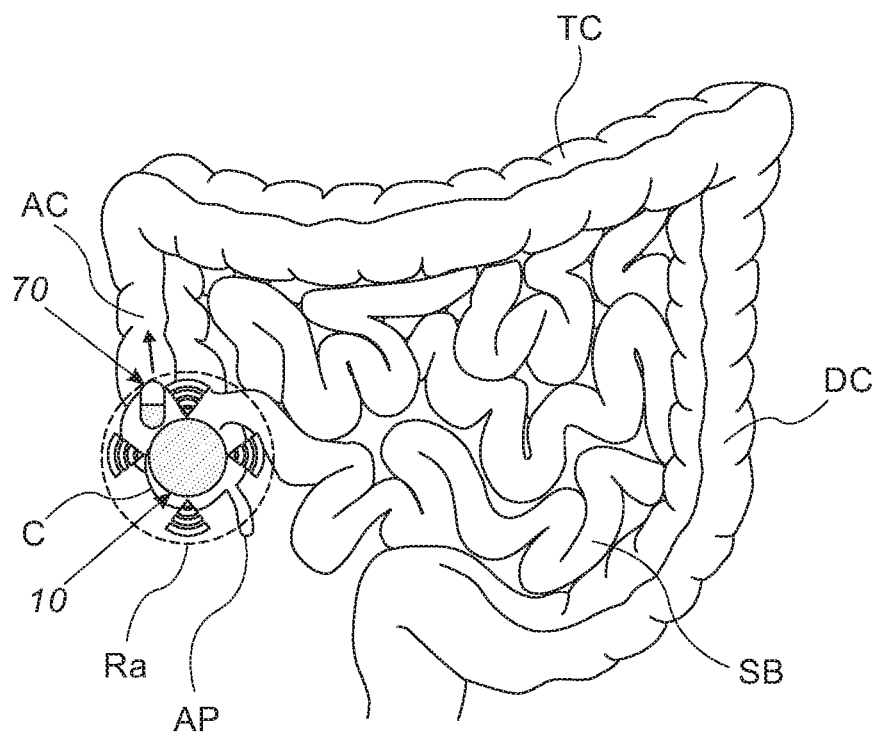
Figure 3D:
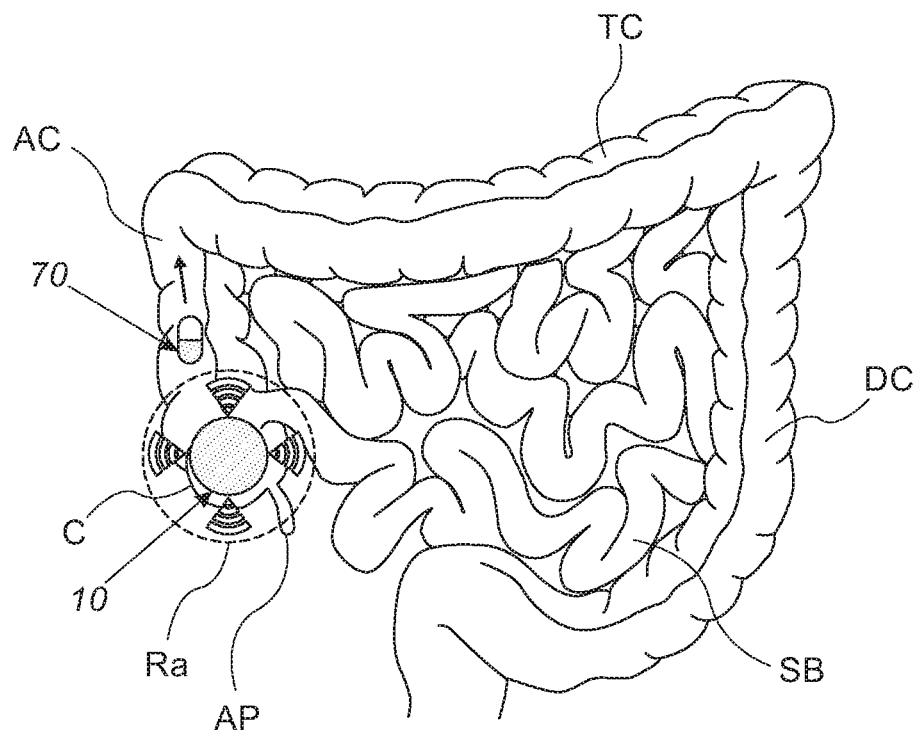
Figure 4A:
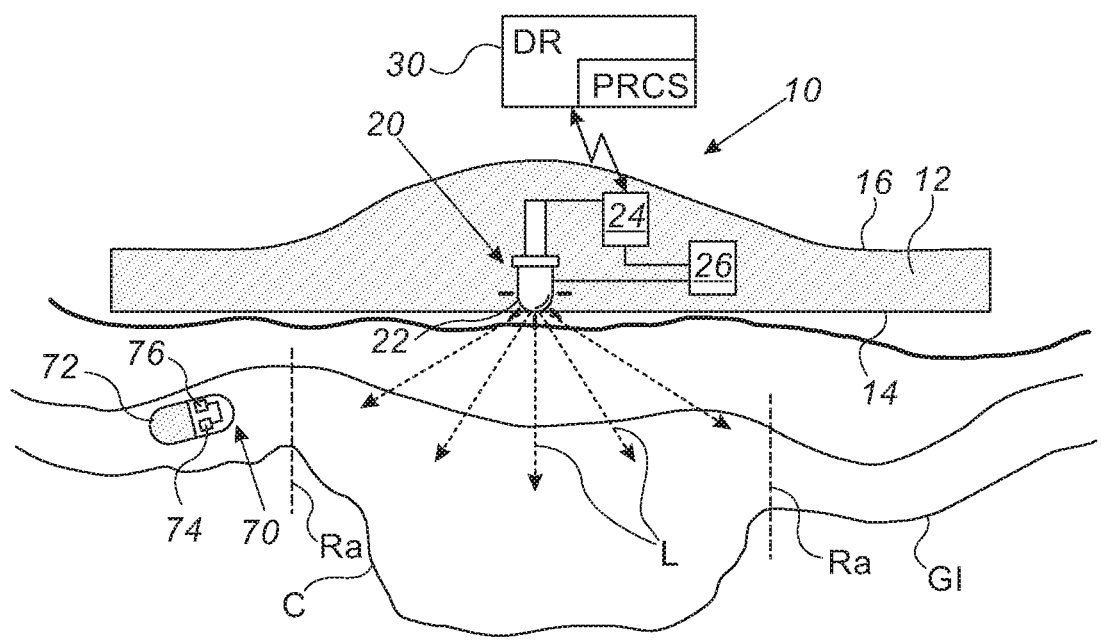
FIGS. 4A to 4D are schematic cross-section views of a portion of the GI tract fitted, externally, with the ex-vivo module of FIG. 2, shown in different stages of progression of the in-vivo device, corresponding to the stages shown in FIGS. 3A to 3D, according to an embodiment of the present invention.
Figure 4B:
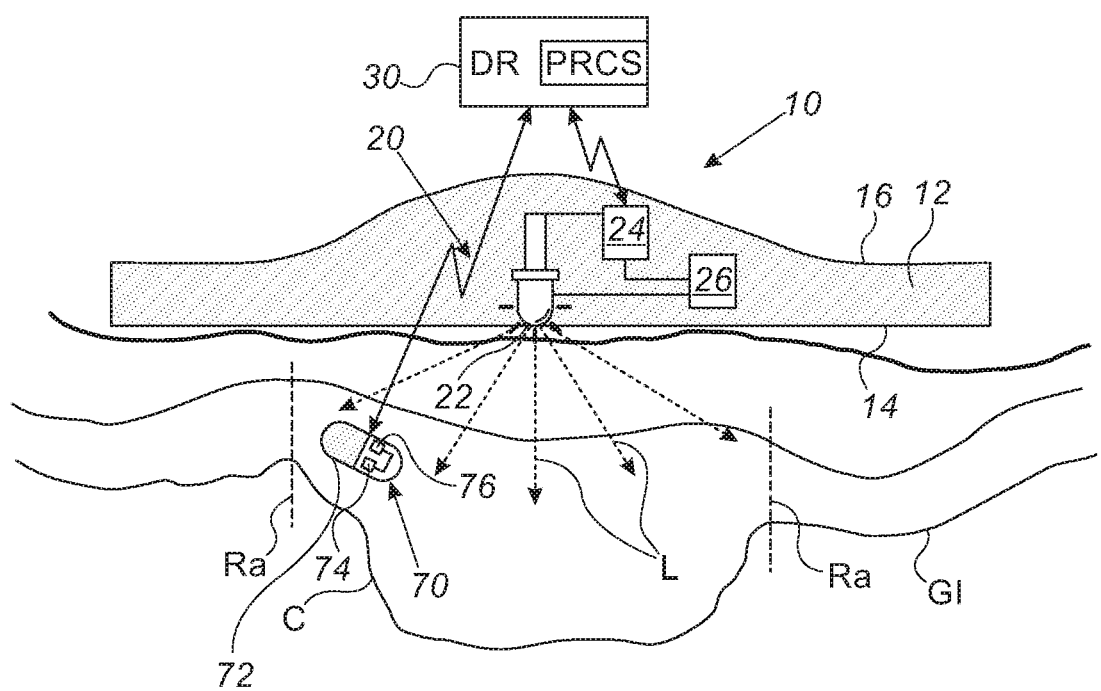
Figure 4C:
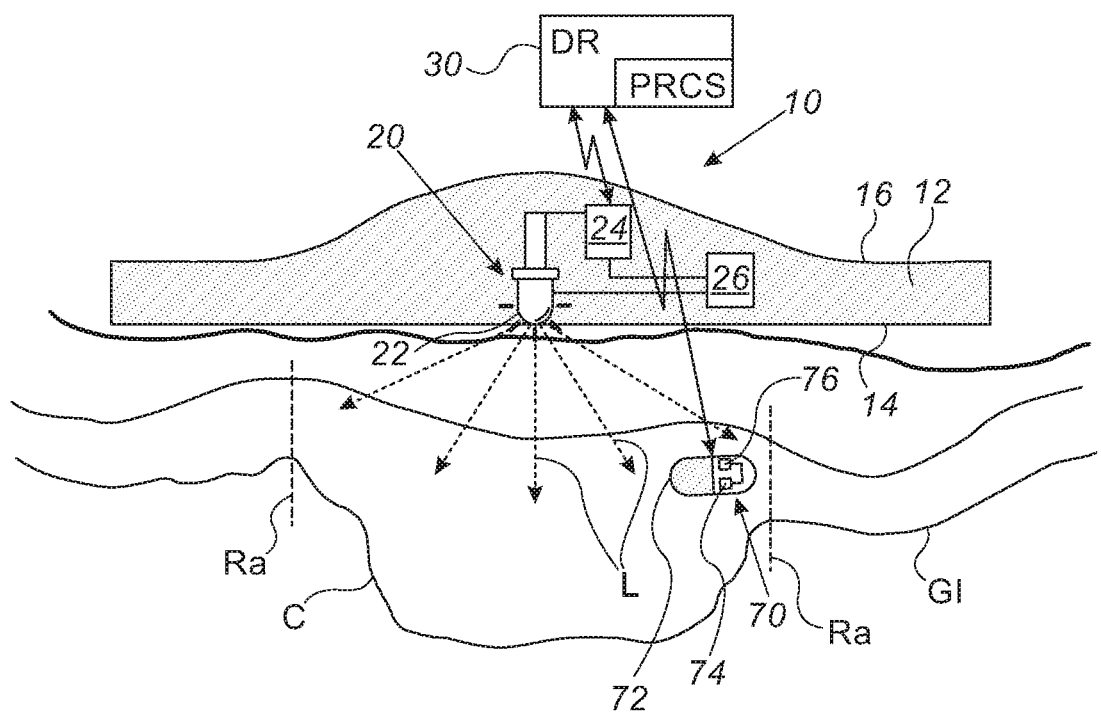
Figure 4D:
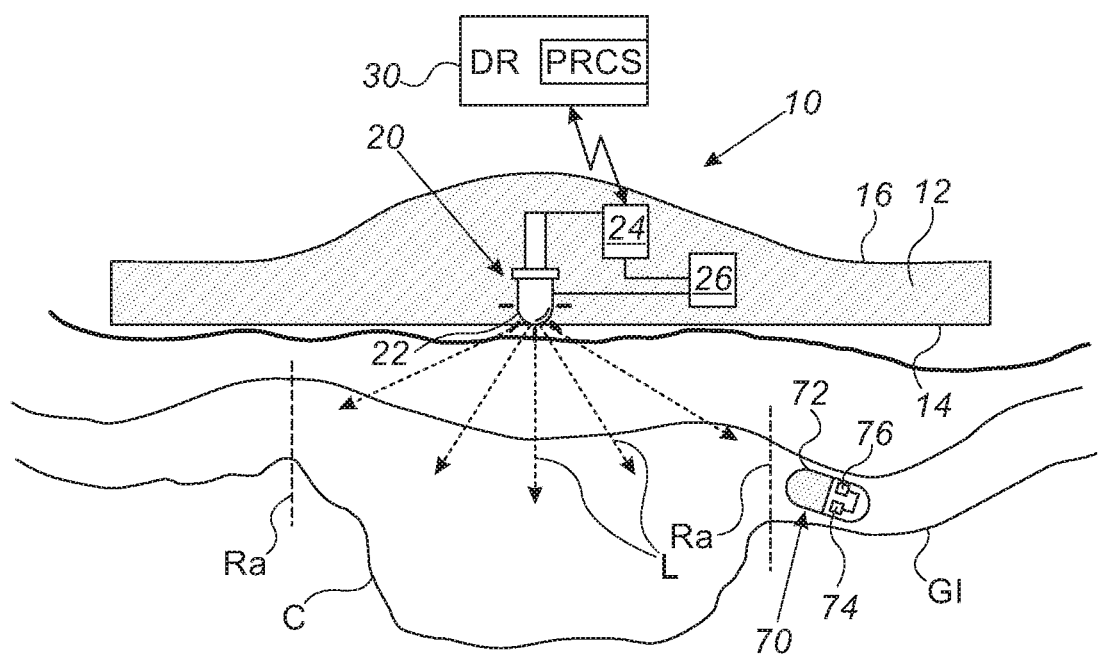

In FIGS. 3A to 3D, respective FIGS. 4A to 4D, and FIG. 7, an example human digestive system is shown with an in-vivo device 70, comprising a sensor 74 and a transmitter 76 shown on FIG. 4A, located therein and progressing therealong in the direction of the arrow. The ex-vivo module 10 is shown being placed externally on the body at a location approximately corresponding to the cecum, and the light L emitted from the LED 22 of the ex-vivo module has a range Ra configured to cover a slightly greater area than the cecum.

In the position shown in FIG. 3A, the capsule 70 is in the small bowel (SB), still out of the range Ra of the ex-vivo module 10. In this position, the light L emitted from the LED 22 cannot be detected by the sensor 74 within the capsule 70, and so the transmitter 76 of the capsule does not produce an alert signal. In this position, the ex-vivo module 10 does not receive an alert signal, and therefore deduces that the capsule 70 has not yet reached the cecum.

In the position shown in FIG. 3B, the in-vivo module 70 is in the range Ra of the light emitted from the LED and therefore the light L emitted from the LED 22 is detected by the sensor 74, which alerts the transmitter 76 of the capsule to produce an alert signal to the DR 30. This alert signal is received by the DR which thereby deduces that the capsule has reached the cecum. This provides a critical indication for diagnostic purposes, allowing a precise pin-pointing of the location of the capsule 70 at a given time.

It is noted that the ex-vivo module 10 can be connected to a data recorder 30, which is configured for receiving data from the ex-vivo module 10 and processing it to determine location/position of the capsule 70.

Since portions of the SB may overlap with the cecum (be located behind it or very close to it), it is possible that the capsule 70, when passing through such a portion of the SB, will sense a certain amount of light L emitted from the LED reaching the SB portion. In this case, the processor PRCS can be configured for registering and analyzing this data, e.g. by duration and/or intensity of the captured light, or by analyzing the imager data (in case the capsule further includes an imager as detailed with regards to another example of a capsule) and, once the capsule actually reaches the cecum, process the data and deduce that the first alert signals received from the capsule 70 were false, and were sent when the capsule 70 was still in the aforementioned SB portion and not in the cecum.

Turning to FIG. 3C, as long as the capsule is within the range Ra of the ex-vivo module 10, it will continue detecting the light L and transmitting an alert signal to be received by the ex-vivo device 10. This can provide an indication not only regarding the position of the capsule 70 within the GI tract, but also provide essential information regarding the time it requires for the capsule 70 to pass through a given portion of the GI tract (in this case the cecum). The time required for the capsule 70 to pass through a given portion of the GI tract can be indicative of various medical conditions of the patient.

As shown in FIGS. 4A to 4D, once the capsule 70 is in range Ra, the sensor 74 can detect light L and command the transmitter 76 to issue an alert signal to the communication unit 24. The communication unit 24, in turn, will provide this data to the data recorder 30 as long as such data is provided to it.

It is noted from FIGS. 4A to 4D, that the ex-vivo module 10 is fitted to the skin S of the patient, so that the light rays L are directed into the patient.

Figure 7:
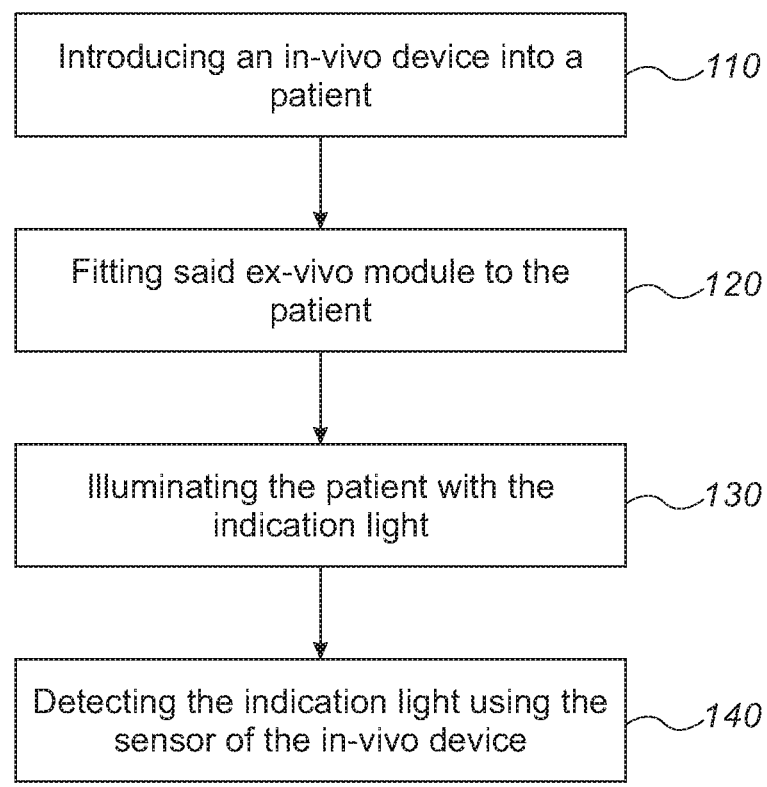
FIG. 7 is schematic block diagram of the method of the present invention according to one embodiment.

With particular reference being made to FIG. 7, an embodiment of the present application includes a method of detecting the position of an in-vivo device using external light. Once an in-vivo device is introduced into the patient 110, the method includes a step of fitting the patient with an ex-vivo module 120 configured for performing the following step which is illuminating the patient with an external indication light 130. The sensor on board the in-vivo device performs the next step of the method which includes detecting the indication light 140.

It is appreciated that steps 130 and 140 of the above described method can be performed repeatedly and/or continuously in order to respectively obtain periodical and/or continuous information on the position of the in-vivo device.

In accordance with another embodiment of the present invention, the capsule 70 may include an imager, which is configured for capturing images throughout its progression along the GI tract, and transmit these images to the communication unit 24. In such case, while the capsule 70 can also include a sensor 74 for detecting the light L from the ex-vivo module 10, it is possible to detect such light using the imager alone, not requiring an additional sensor.

In particular, external light can affect the images captured by the in-vivo device 70, in what is called a 'halo' effect—creating a halo of light around the captured image. Thus, the processor can be configured for identifying captured images containing such a 'halo' effect in order to indicate if the capsule 70 indeed reached the location corresponding to that of the ex-vivo module 10.

It is known that the progression of the in-vivo device through the cecum is considerably more rapid that its progression along the small intestine. As such, it may be desired to perform for example:

In case of capsules configured for imaging of the colon—start capturing the images in the cecum (since the imager was not configured for capturing images while in the small intestine); and In case of capsules configured for imaging of both the small bowel and the colon, e.g. capsules which were already obtaining images of the small bowel before being detected by the system, increase the frame rate of image capture when the capsule 70 is at the area of the cecum. Specifically, if the in-vivo device 70 is configured for capturing images at a base rate FR1, it may be desired to increase this frame rate to FR2>FR1, when the capsule 70 reaches the cecum.

Thus, if the ex-vivo module 10 is properly positioned at the area of the cecum, in accordance with the above example, operations such as the following may occur:

i. Initially, the capsule 70 senses the external light by imager, or captures images at a frame rate FR1 containing a halo effect;

ii. the obtained images are transferred to the processor;

iii. the processor identifies the external light or the halo effect and deduces that the capsule 70 has reached the cecum. Identification can be performed, for example, by comparing the light measurement to an intensity threshold or by image analysis;

iv. the processor issues an alert signal to the capsule 70 either to start capturing the images or to switch to a second frame rate FR2;

v. the capsule proceeds to capture images at the second (faster) rate;

It is noted that during the passage of the capsule 70 through the cecum, the light L can be switched off, at least periodically, in order to prevent damaging of the images captured in the cecum by the halo effect.

It is appreciated that, in case the capsule 70 has an on-board imaging system configured for obtaining images of the GI tract, such a system can also comprise an illumination source as known per se (not shown). Thus, in accordance with a specific example, the DR 30, the LED 22 and illumination source of the imaging system of the capsule 70 can all be synchronized so that when the illumination source is switched on to facilitate obtaining an image of the GI tract, the LED 22 is respectively switched off in order to prevent, for example, a halo effect in the obtained image.

Synchronizing the lighting of the LED 22 and the illumination source can be controlled by the DR 30, and at least the two following configurations are possible:

a) Only the illumination source of the capsule 70 is controlled by the DR 30. In this case, the LED 22 operates at a constant lighting rate which is known to the DR 30 (but is not controlled thereby), and the DR 30 is configured for switching the illumination source of the capsule 70 on and off in correlation with the LED 22; and b) Both the LED 22 and the illumination source of the capsule 70 are controlled by the DR 30 which makes sure that these light sources are not switched on simultaneously.

When the capsule 70 leaves the area of the cecum, for example in a process reverse to the described above, the frame rate can be switched back to FR1, or to any other frame rate specifically designed for capturing images in the colon.

Alternatively, in accordance with another example, the imager of the in-vivo module 70 can be configured for dual-use—a main use as an imager and a secondary use as a light sensor. Specifically, it is appreciated that the imager of the in-vivo module 70 may have no shutter, e.g. each time it is required to acquire a new image, the image sensor needs to be electronically 'wiped' clean. This is performed in a given frequency in accordance with the requirements of the in-vivo device.

In accordance with one embodiments, it is suggested, in the intervals between acquisition of images by the imager, to perform an additional 'wipe' of the image sensor, and using it merely for detecting the presence of light. In other words, the imager in one embodiment operates at two alternating modes:

Image acquisition mode—the sensor is 'wiped' a first time and an image is acquired; and Light sensing mode—the sensor is 'wiped' a second time and only the presence of light over a predetermined threshold is recorder. It is important to note that in this mode, no image is provided by the imager to the data recorder 30. Instead, the data recorder 30 only receives a yes/no alert signal regarding the presence of light above a predetermined threshold.

Figure 1B:
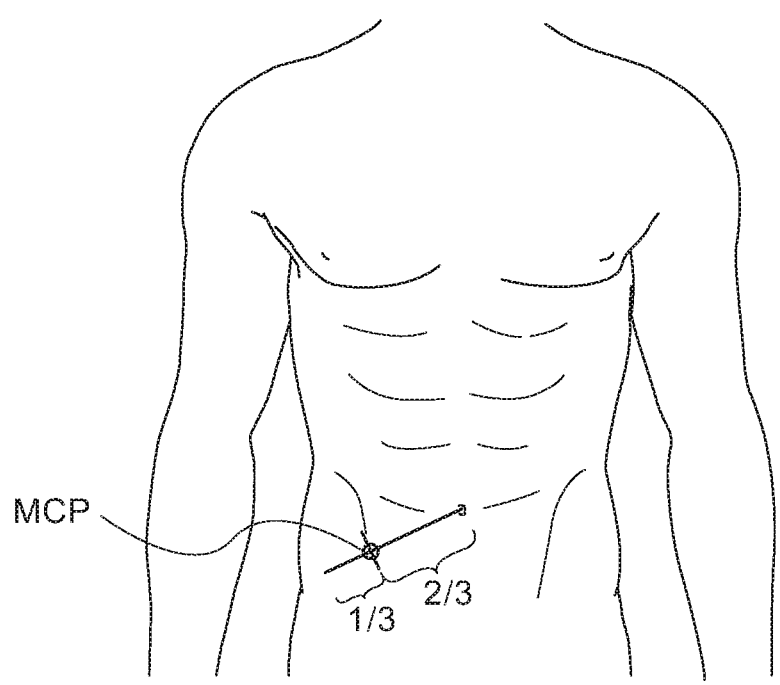
FIG. 1B is a schematic view of the human abdominal portion with an indication of the location of McBurney's point.

With additional reference being made to FIGS. 1A and 1B, in order to properly locate the ex-vivo module 10 at an area corresponding to the cecum, one embodiment is based on appendicitis diagnosis. In FIG. 1A, a basic diagram of the GI tract is shown, including the small bowel SB, cecum C, ascending colon AC, transverse colon TC and descending colon DC. Specifically, since the appendix and the cecum are proximal to each other, embodiments of the present invention may bring forth the concept of identifying the location of the appendix as an indication to the position of the cecum. In order to do this, one of the common methods for locating the position of the appendix is based on the concept of McBurney's point, a point located at the ⅓ of the way between the navel and the hip bone. Thus, positioning the ex-vivo module 10 there, will also give an indication to the position of the cecum.

With reference now being made to FIG. 5, it may be desired to slow down the progression of the capsule 70 through the cecum. In accordance with another embodiment of the present invention, the ex-vivo patch 10 can also include a progress regulating component 40 which is configured, once the processor 24 indicates that the capsule 70 is in the range of the ex-vivo patch 10, to act on the capsule 70 in order to stop/slow down its progression within the GI tract. One example of a progress regulating component 40 is a magnetic component (e.g. an electromagnetic coil) configured for magnetically holding the capsule 70 (which may contain any magnetic material, e.g. batteries) through the skin of the patient in order to prolong its stay in the cecum. The progress regulating component 40 can also draw power from the power source 26, and be in communication with the communication unit 24 to receive alert signals therefrom.

With addition reference being made to FIG. 6, the monitoring system can be designed as a wearable belt 50 mounted over the waist of the patient, the belt including the ex-vivo module 10 and the DR 30. It is noted that the ex-vivo module 10 is installed on the inner side of the belt 50, such that when the belt is mounted onto the patient, the contact surface 14 is exposed and is facing the patient's skin.

Those skilled in the art to which this invention pertains will readily appreciate that numerous changes, variations, and modifications can be made without departing from the scope of the invention, mutatis mutandis.

Descriptions of embodiments of the invention in the present application are provided by way of example and are not intended to limit the scope of the invention. The described embodiments comprise different features, not all of which are required in all embodiments. Some embodiments utilize only some of the features or possible combinations of the features. Variations of embodiments of the invention that are described, and embodiments comprising different combinations of features noted in the described embodiments, will occur to a person having ordinary skill in the art. The scope of the invention is limited only by the claims.

Unless explicitly stated, the method embodiments described herein are not constrained to a particular order in time or chronological sequence. Additionally, some of the described method elements may be skipped, or they may be repeated, during a sequence of operations of a method.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A system for detecting position of an in-vivo device based on external light, the system comprising:
    an adhesive ex-vivo module configured to be positioned outside a body and configured to adhere to a location of skin of the body, the adhesive ex-vivo module comprising at least one illumination source configured to emit light towards the body through the skin of the body; and
    an in-vivo device configured to operate inside the body, the in-vivo device comprising:
        at least one sensor configured to, while operating inside the body, sense the light emitted through the skin of the body by the at least one illumination source,
        an in-vivo communication device,
        wherein the in-vivo communication device is configured to communicate an alert signal to a communication device outside the body in response to the at least one sensor sensing the light emitted through the skin of the body by the at least one illumination source, the alert signal indicative of a position of the in-vivo device in the body relative to the adhesive ex-vivo module, and
        an imager configured for obtaining in-vivo images,
        wherein the in-vivo device is configured for obtaining the in-vivo images in a first operational mode and for switching to obtaining the in-vivo images in a second operational mode when the at least one sensor detects the light emitted through the skin of the body by the at least one illumination source.

2. A system according to claim 1, wherein the adhesive ex-vivo module is in the form of a patch.

3. A system according to claim 2, wherein the patch has a contact surface configured for facing the body when fitted thereto, and wherein the at least one illumination source has at least one light emitting point located on the contact surface.

4. A system according claim 1, wherein the first and second operational modes differ from one another in the frame rate of capturing images such that, in the first operational mode, the in-vivo device captures in-vivo images at a first frame rate, and in the second operational mode, the in-vivo device captures in-vivo images in a second frame rate different from the first frame rate.

5. A system according to claim 1, wherein the in-vivo device is configured for commencing imaging when the at least one sensor detects the light.

6. A system according to claim 1, wherein the in-vivo device comprises an on-board illumination source configured for providing light for obtaining images by the imager, and wherein the on-board illumination source and the at least one illumination source of the adhesive ex-vivo module are synchronized such that their lighting time does not fully overlap.

7. A system according to claim 1, further comprising a progress regulating component configured for at least one of: slowing down or stopping the in-vivo device at a certain location.

8. A system according to claim 7, wherein the progress regulating component is configured for using magnetic forces to perform the slowing down or stopping the in-vivo device at a certain location.

9. A system according to claim 7, wherein the progress regulating component constitutes part of the adhesive ex-vivo module.

10. A method for detecting position of an in-vivo device based on external light using an adhesive ex-vivo module positioned outside a body of a patient and adhered to a location of skin of the body and based on using the in-vivo device operating inside the body, the in-vivo device comprising an imager configured for obtaining in-vivo images, the method comprising:
    illuminating the patient with light emitted, by at least one illumination source of the adhesive ex-vivo module, towards the body through the skin of the body;
    detecting the light emitted through the skin of the body by the at least one illumination source using at least one sensor of the in-vivo device inside the patient;
    in response to the at least one sensor sensing the light emitted through the skin of the body by the at least one illumination source, communicating an alert, by an in-vivo communication device of the in-vivo device, to a communication device outside the body, the alert indicative of a position of the in-vivo device in the body relative to the adhesive ex-vivo module; and
    obtaining the in-vivo images in a first operational mode before detection of the light, and switching to obtaining the in-vivo images in a second operational mode upon detection of the light emitted through the skin of the body by the at least one illumination source.

11. A system according to claim 1, wherein the adhesive ex-vivo module comprises an operative contact surface configured for facing a patient when fitted thereto, and the at least one illumination source is configured for emitting the light at a predetermined wavelength range, wherein the at least one illumination source is facing in a same direction as the contact surface.

12. A system according to claim 1, wherein the at least one sensor is an imager capable of obtaining in-vivo images inside the body, wherein the in-vivo device does not include another light sensor separate from the imager.

13. A system according to claim 12, wherein the imager alternates between an image acquisition mode configured to capture in-vivo images and a light sensing mode configured to sense the light emitted through the skin of the body by the at least one illumination source.

* * * * *